United States Patent
Govari

(10) Patent No.: US 8,852,130 B2
(45) Date of Patent: *Oct. 7, 2014

(54) CATHETER WITH STRAIN GAUGE SENSOR

(71) Applicant: Biosense Webster (Israel) Ltd., New Brunswick, NJ (US)

(72) Inventor: Assaf Govari, Haifa (IL)

(73) Assignee: Biosense Webster (Israel), Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,125

(22) Filed: Sep. 9, 2013

(65) Prior Publication Data
US 2014/0024970 A1    Jan. 23, 2014

Related U.S. Application Data

(63) Continuation of application No. 12/647,824, filed on Dec. 28, 2009, now Pat. No. 8,529,476.

(51) Int. Cl.
*A61B 5/00* (2006.01)

(52) U.S. Cl.
USPC ............................................... 600/595

(58) Field of Classification Search
USPC ................................. 600/587, 595
See application file for complete search history.

(56) References Cited

U.S. PATENT DOCUMENTS

| | | | |
|---|---|---|---|
| 3,841,150 A * | 10/1974 | Pearson | 73/766 |
| 3,971,364 A | 7/1976 | Fletcher et al. | |
| 4,764,114 A | 8/1988 | Jeffcoat et al. | |
| 4,856,993 A | 8/1989 | Maness et al. | |
| 4,930,494 A | 6/1990 | Takehana et al. | |
| 5,263,493 A | 11/1993 | Avitall | |
| 5,368,564 A | 11/1994 | Savage | |
| 5,391,199 A | 2/1995 | Ben Haim | |
| 5,462,527 A | 10/1995 | Stevens-Wright et al. | |
| 5,487,757 A | 1/1996 | Truckai et al. | |
| 5,499,542 A | 3/1996 | Morlan | |
| 5,542,434 A | 8/1996 | Imran et al. | |
| 5,558,091 A | 9/1996 | Acker et al. | |

(Continued)

FOREIGN PATENT DOCUMENTS

| DE | 19750441 A | 6/1999 |
|---|---|---|
| EP | 928601 A1 | 7/1999 |

(Continued)

OTHER PUBLICATIONS

Biter, William J. et al., "Magnetic Wire Strain Sensor", 33rd International Sampe Technical Conference, Nov. 5-8, 2001, vol. 33, pp. 12-23, Seattle, WA.

(Continued)

*Primary Examiner* — Max Hindenburg

(57) ABSTRACT

A medical probe, including a flexible insertion tube, having a distal end for insertion into a body cavity of a patient and which is configured to be brought into contact with tissue in the body cavity. The probe further includes a sensor tube of an elastic material, contained inside the distal end of the insertion tube and configured to deform in response to forces exerted by the tissue on the distal end. The probe also includes a plurality of strain gauges fixedly attached to a surface of the sensor tube at different, respective locations and configured to generate respective signals in response to deformations of the sensor tube.

20 Claims, 4 Drawing Sheets

(56) References Cited

U.S. PATENT DOCUMENTS

| | | |
|---|---|---|
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,728,149 A | 3/1998 | Laske et al. |
| 5,769,843 A | 6/1998 | Abela et al. |
| 5,826,576 A | 10/1998 | West |
| 5,833,608 A | 11/1998 | Acker |
| 5,836,894 A | 11/1998 | Sarvazyan |
| 5,860,974 A | 1/1999 | Abele |
| 5,861,024 A | 1/1999 | Rashidi |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,974,320 A | 10/1999 | Ward et al. |
| 5,983,126 A | 11/1999 | Wittkampf |
| 6,048,329 A | 4/2000 | Thompson et al. |
| 6,063,022 A | 5/2000 | Ben Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,266,551 B1 | 7/2001 | Osadchy et al. |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,334,837 B1 | 1/2002 | Hein |
| 6,335,617 B1 | 1/2002 | Osadchy et al. |
| 6,351,549 B1 | 2/2002 | Souluer |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,569,098 B2 | 5/2003 | Kawchuk |
| 6,574,492 B1 | 6/2003 | Ben Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben Haim et al. |
| 6,695,808 B2 | 2/2004 | Tom |
| 6,711,429 B1 | 3/2004 | Gilboa et al. |
| 6,727,371 B2 | 4/2004 | Müller et al. |
| 6,814,733 B2 | 11/2004 | Schwartz et al. |
| 6,835,173 B2 | 12/2004 | Couvillon, Jr. |
| 6,892,091 B1 | 5/2005 | Ben Haim et al. |
| 6,915,149 B2 | 7/2005 | Ben Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,077,823 B2 | 7/2006 | McDaniel |
| 7,156,816 B2 | 1/2007 | Schwartz et al. |
| 7,235,070 B2 | 6/2007 | Vanney |
| 7,297,116 B2 | 11/2007 | Varghese et al. |
| 7,306,593 B2 | 12/2007 | Keidar et al. |
| 7,306,599 B2 | 12/2007 | Karasawa et al. |
| 7,311,704 B2 | 12/2007 | Paul et al. |
| 7,397,364 B2 | 7/2008 | Govari |
| 7,435,232 B2 | 10/2008 | Liebschner |
| 7,465,288 B2 | 12/2008 | Dudney et al. |
| 7,481,774 B2 | 1/2009 | Brockway et al. |
| 7,536,218 B2 | 5/2009 | Govari et al. |
| 7,604,605 B2 | 10/2009 | Zvuloni |
| 7,662,151 B2 | 2/2010 | Crompton, Jr. et al. |
| 7,681,432 B2 | 3/2010 | Hay et al. |
| 7,686,767 B2 | 3/2010 | Maschke |
| 7,914,440 B2 | 3/2011 | Otawara |
| 7,959,601 B2 | 6/2011 | McDaniel et al. |
| 7,984,659 B2 | 7/2011 | Fujimoto et al. |
| 8,043,216 B2 | 10/2011 | Matsumura |
| 8,046,049 B2 | 10/2011 | Govari et al. |
| 8,083,691 B2 | 12/2011 | Goldenberg et al. |
| 8,137,275 B2 | 3/2012 | Fan et al. |
| 8,374,819 B2 | 2/2013 | Govari et al. |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0065455 A1 | 5/2002 | Ben Haim et al. |
| 2002/0068866 A1 | 6/2002 | Zikorus et al. |
| 2002/0068931 A1 | 6/2002 | Wong et al. |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0187389 A1 | 10/2003 | Morency et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 | 5/2004 | Hunter et al. |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0080429 A1 | 4/2005 | Freyman et al. |
| 2005/0096590 A1 | 5/2005 | Gullickson et al. |
| 2005/0228274 A1 | 10/2005 | Boese et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0064038 A1 | 3/2006 | Omata et al. |
| 2006/0074297 A1 | 4/2006 | Viswanathan |
| 2006/0173480 A1 | 8/2006 | Zhang |
| 2006/0184106 A1 | 8/2006 | McDaniel et al. |
| 2006/0200049 A1 | 9/2006 | Leo et al. |
| 2006/0247618 A1 | 11/2006 | Kaplan et al. |
| 2007/0021742 A1 | 1/2007 | Viswanathan |
| 2007/0060832 A1 | 3/2007 | Levin |
| 2007/0060847 A1 | 3/2007 | Leo et al. |
| 2007/0100332 A1* | 5/2007 | Paul et al. ........................ 606/41 |
| 2007/0106114 A1 | 5/2007 | Sugimoto et al. |
| 2007/0106165 A1 | 5/2007 | Tulkki |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0167740 A1 | 7/2007 | Grunewald et al. |
| 2007/0167818 A1 | 7/2007 | Osborn et al. |
| 2007/0167819 A1 | 7/2007 | Osborn, III et al. |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0233044 A1 | 10/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0183075 A1 | 7/2008 | Govari et al. |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsumura |
| 2008/0275428 A1 | 11/2008 | Tegg et al. |

(56) References Cited

U.S. PATENT DOCUMENTS

| | | |
|---|---|---|
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306650 A1 | 12/2009 | Govari et al. |
| 2010/0063478 A1* | 3/2010 | Selkee .......................... 604/524 |
| 2010/0069921 A1 | 3/2010 | Miller et al. |
| 2010/0121138 A1 | 5/2010 | Goldenberg et al. |
| 2010/0137845 A1 | 6/2010 | Ramstein et al. |
| 2010/0152574 A1 | 6/2010 | Erdman et al. |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2047797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 2000126301 A | 5/2000 |
| JP | 2000508224 A | 7/2000 |
| JP | 2005040215 | 2/2005 |
| JP | 2005237964 A | 9/2005 |
| JP | 2005345215 A | 12/2005 |
| JP | 2006064465 A | 3/2006 |
| JP | 2006255401 A | 9/2006 |
| JP | 2007181696 A | 7/2007 |
| WO | WO 94/17856 A1 | 8/1994 |
| WO | WO 95/10326 A | 4/1995 |
| WO | WO 96/05768 A | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 03/020139 A | 3/2003 |
| WO | WO 2006/029563 A | 3/2006 |
| WO | WO 2006/086152 A | 8/2006 |
| WO | WO 2006/092563 A | 9/2006 |
| WO | WO 2006/135483 A2 | 12/2006 |
| WO | WO 2007/015139 A2 | 2/2007 |
| WO | WO 2007/025230 A | 3/2007 |
| WO | WO 2007/050960 A | 5/2007 |
| WO | WO 2007/067938 A | 6/2007 |
| WO | WO 2007/076312 A2 | 7/2007 |
| WO | WO 2007/082216 A | 7/2007 |
| WO | WO 2007/098494 A1 | 8/2007 |
| WO | WO 2007/111182 A | 10/2007 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |
| WO | WO 2011/046874 A1 | 4/2011 |

OTHER PUBLICATIONS

Biter, William J. et al., "Magnetic Wire for Monitoring Strain in Composites", *Sensors*, Jun. 2001, www.sensormag.com, pp. 110-114.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

Instron Marketing Brochure, "Medical Device Testing Systems", Instron 2007 http://web.archive.org/web/20080318092822/http://www.instron.com.tr/wa/library/streamfile.aspx?doc=1678 &downland=true.

Instron, "Series 3300 Load Frames, Reference Manual Equipment", Instron, pp. 1-5 and 1-10, 2004

Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).

Okumura, M.D. Yasuo et al. "A Systematic Analysis of In Vivo Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.

Peirs, J. et al., "Design of an Optical Force Sensor for Force Feedback during Minimally Invasive Robotic Surgery", Eurosensors XVII, 2003, pp. 1063-1066, http:/ /mech.kuleuven.be/micro/pub/medic/Paper_Eurosensors_2003_MIS_sensor_extended.pdf.

Partial European Search Report mailed on Sep. 18, 2009 from related European Patent Application No. 08253265.6.

Partial European Search Report mailed on Dec. 7, 2009 from related European Patent Application No. 09251502.2.

European Search Report mailed on Mar. 8, 2010 from related European Patent Application No. 09252143.4.

Partial European Search Report mailed on Mar. 29, 2010 from related European Patent Application No. 09252879.3.

Partial European Search Report mailed on Apr. 1, 2010 from related European Patent Application No. 09252721.7.

European Search Report mailed on Mar. 2, 2011 from related European Patent Application No. 10175931.4.

(56) References Cited

OTHER PUBLICATIONS

European Search Report mailed on Mar. 28, 2011 from related European Patent Application No. 10252189.5.
European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from corresponding European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Sep. 23, 2011 from related European Patent Application No. 11169251.3.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

\* cited by examiner

CATHETER WITH STRAIN GAUGE SENSOR

CROSS REFERENCE TO RELATED APPLICATION

This application is a continuation of, and claims priority to, U.S. application Ser. No. 12/647,824, now U.S. Pat. No. 8,529,476, filed on Dec. 28, 2009, which is incorporated in its entirety herein by explicit reference.

FIELD OF THE INVENTION

The present invention relates generally to invasive medical devices, and specifically to the construction of probes for insertion into body organs.

BACKGROUND OF THE INVENTION

In some diagnostic and therapeutic techniques, a catheter is inserted into a chamber of the heart and is brought into contact with the inner heart wall. In such procedures, it is generally important that the distal tip of the catheter engages the endocardium with sufficient pressure to ensure good contact. Excessive pressure, however, may cause undesired damage to the heart tissue and even perforation of the heart wall.

For example, in intracardiac radio-frequency (RF) ablation, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. Proper contact between the electrode and the endocardium during ablation is necessary in order to achieve the desired therapeutic effect without excessive damage to the tissue.

A number of patent publications describe catheters with integrated pressure sensors for sensing tissue contact. As one example, U.S. Patent Application Publication 2007/0100332 to Saurav et al., whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

The description above is presented as a general overview of related art in this field and should not be construed as an admission that any of the information it contains constitutes prior art against the present patent application.

SUMMARY OF THE INVENTION

An embodiment of the present invention provides a medical probe, including:

a flexible insertion tube, having a distal end for insertion into a body cavity of a patient and which is configured to be brought into contact with tissue in the body cavity;

a sensor tube including an elastic material, contained inside the distal end of the insertion tube and configured to deform in response to forces exerted by the tissue on the distal end; and a plurality of strain gauges fixedly attached to a surface of the sensor tube at different, respective locations and configured to generate respective signals in response to deformations of the sensor tube.

Typically, the sensor tube is fixedly attached inside the distal end to the insertion tube, and the surface of the sensor tube may include an outer curved surface of the sensor tube.

In one embodiment the respective signals are configured to generate a magnitude and a direction of a pressure on a termination of the distal end. Alternatively or additionally, the respective signals are configured to generate a magnitude and a direction of a deflection of a termination of the distal end.

The plurality of strain gauges may be symmetrically disposed with respect to an axis of the sensor tube, and additionally may be positioned on a circumference of the surface of the sensor tube, wherein the circumference is centrally located with respect to the sensor tube.

In a disclosed embodiment the plurality of strain gauges have respective gauge directions, and the gauges are fixedly attached to the surface of the sensor tube so that the respective gauge directions are parallel to an axis of the sensor tube.

In a further disclosed embodiment the probe includes at least one temperature-compensating strain gauge configured to generate signals to compensate for changes in temperature of the plurality of strain gauges. The at least one temperature-compensating strain gauge may be mounted on a block having a block-thermal mass, and the sensor tube may have an assembly-tube-thermal mass equal to the block-thermal mass.

The at least one temperature-compensating strain gauge may be mounted on the block in a location that does not deform in response to deformations of the sensor tube.

The at least one temperature-compensating strain gauge may have a temperature-compensating strain gauge direction configured to be orthogonal to an axis of the sensor tube.

There is further provided, according to a disclosed embodiment of the present invention, a method for producing a medical probe, including:

providing a flexible insertion tube, having a distal end for insertion into a body cavity of a patient and which is configured to be brought into contact with tissue in the body cavity;

installing a sensor tube including an elastic material inside the distal end of the insertion tube, the sensor tube being configured to deform in response to forces exerted by the tissue on the distal end; and fixedly attaching a plurality of strain gauges to a surface of the sensor tube at different, respective locations, the strain gauges being configured to generate respective signals in response to deformations of the sensor tube.

There is further provided, according to a disclosed embodiment of the present invention, apparatus for performing a medical procedure, including:

a medical probe, including:

a flexible insertion tube, having a distal end for insertion into a body cavity of a patient and which is configured to be brought into contact with tissue in the body cavity;

a sensor tube including an elastic material, contained inside the distal end of the insertion tube and configured to deform in response to forces exerted by the tissue on the distal end; and a plurality of strain gauges fixedly attached to a surface of the sensor tube at different, respective locations and configured to generate respective signals in response to deformations of the sensor tube; and a console, which receives the respective signals from the strain gauges and in response provides an indication of the forces on the distal end.

There is further provided, according to a disclosed embodiment of the present invention, a method for performing a medical procedure, including:

providing a flexible insertion tube, having a distal end for insertion into a body cavity of a patient and which is configured to be brought into contact with tissue in the body cavity;

installing a sensor tube including an elastic material inside the distal end of the insertion tube, the sensor tube being configured to deform in response to forces exerted by the tissue on the distal end;

fixedly attaching a plurality of strain gauges to a surface of the sensor tube at different, respective locations, the strain gauges being configured to generate respective signals in response to deformations of the sensor tube;

receiving the respective signals at a console; and providing at the console an indication of the forces on the distal end in response to receiving the respective signals.

The present invention will be more fully understood from the following detailed description of the embodiments thereof, taken together with the drawings in which:

DETAILED DESCRIPTION OF EMBODIMENTS
OVERVIEW

Embodiments of the present invention provide a novel design of an invasive probe, such as a catheter. The probe comprises a flexible insertion tube for insertion into a body cavity of a patient, and a pressure sensing assembly is installed inside the distal end of the insertion tube. The assembly comprises a tube of elastic material having a plurality of strain gauges fixedly attached to different respective locations of a surface, typically the outer curved surface, of the tube. Typically, three or more strain gauges are fixedly attached to the surface.

When the distal end of the probe engages tissue in the body cavity, force on the end causes the probe to bend and/or compress, and the tube of elastic material to deform. Depending on the magnitude and direction of the force relative to the tube, the deformation of the tube consists of expansion and/or contraction of the locations of the tube's surface to which the strain gauges are attached. The strain gauges provide respective signals in response to the deformation of the locations of the tube to which the gauges are attached, and a processing unit calculates the pressure (caused by the force) on the end, from the strain gauge signals. The processing unit may also calculate a deflection of the end from the signals.

The combination of strain gauges attached to an elastic tube provides a reliable, accurate, pressure sensing device that is simpler and cheaper to manufacture than other pressure sensing devices known in the art.

DETAILED DESCRIPTION OF THE DRAWINGS

Figure 1:
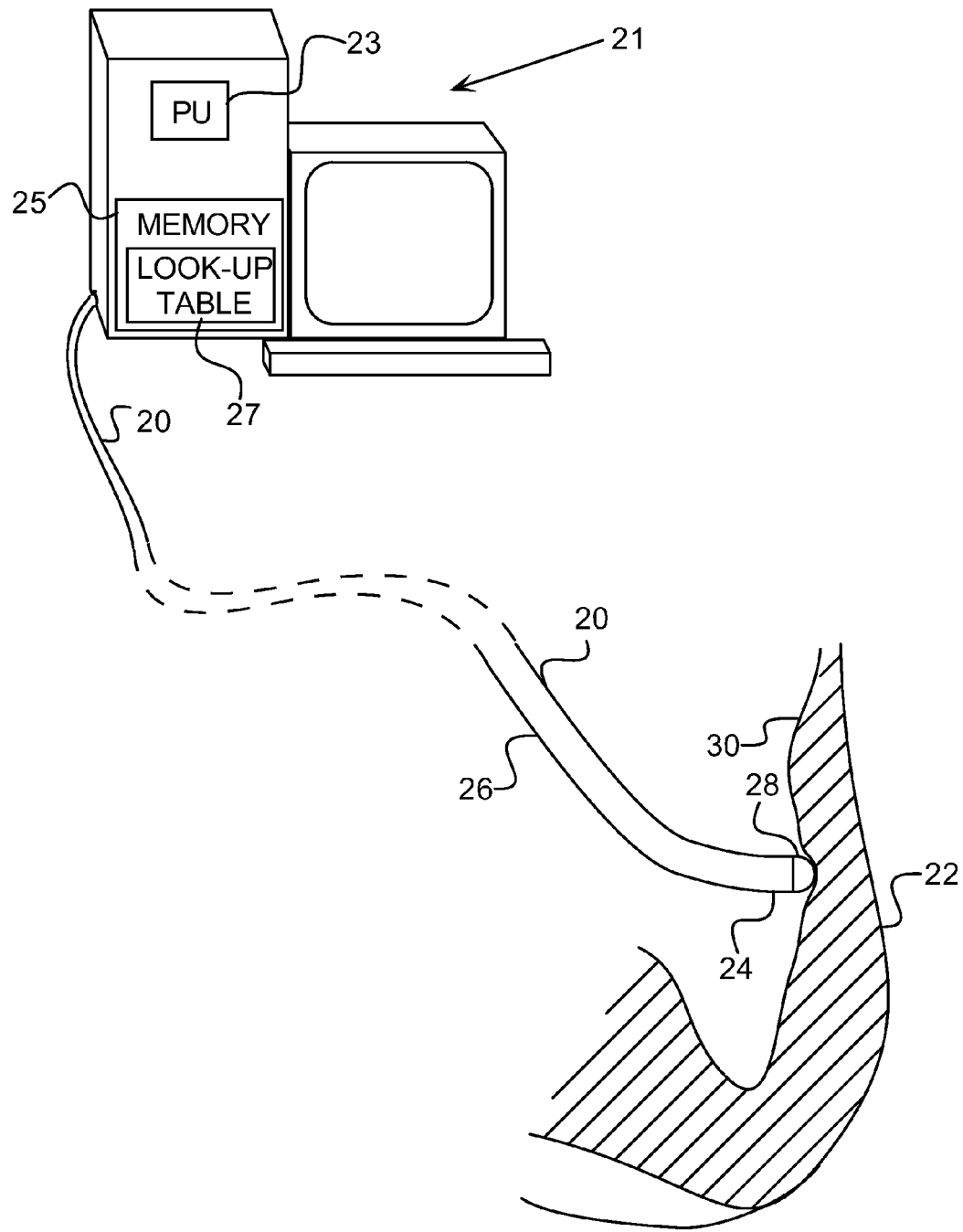
FIG. 1 is a schematic illustration of operation of a catheter, according to an embodiment of the present invention.

FIG. 1 is a schematic illustration of operation of a catheter 20, according to an embodiment of the present invention. As is illustrated in FIG. 1, a proximal end of catheter 20 is coupled to an operating console 21, which is controlled by an operator of the catheter. The operator also manipulates the catheter using controls (not shown) while the catheter is being used to perform a medical procedure. Console 21 comprises a processing unit (PU) 23, which, inter alia, receives and analyzes signals from elements at a distal end of catheter 20. The elements and the signal analysis are described in more detail below. Processing unit 23 uses software stored in a memory 25, the software typically including a look-up table 27, for the signal analysis, as well as for performing other functions related to operation of the catheter. The software may be downloaded to console 21 in electronic form, over a network, for example, or it may, alternatively or additionally, be provided and/or stored on tangible media, such as magnetic, optical, or electronic memory.

Catheter 20 comprises a flexible insertion tube 26. A lower portion of FIG. 1 schematically illustrates a sectional view of a chamber of a heart 22, showing flexible insertion tube 26 of the catheter 20 inside the heart. The catheter is typically inserted into the heart percutaneously through a blood vessel, such as the vena cava or the aorta. A termination 28 of tube 26, fixedly attached to a distal end 24 of the tube, engages endocardial tissue 30. Typically termination 28 comprises an electrode, which may be used for ablation. However, there is no requirement that termination 28 comprises an electrode and the termination may comprise any other element, such as a camera. For simplicity, in the following description termination 28 is assumed to comprise an electrode, and those having ordinary skill in the art will be able to adapt the description, mutatis mutandis, for other types of termination. Force exerted by termination 28 against the endocardium deforms the endocardial tissue locally, and leads to a countervailing force from the endocardium on the termination.

In the pictured example, termination 28 engages the endocardium head-on. The countervailing force causes distal end 24 of insertion tube 26 to compress slightly. Alternatively (not pictured), the termination engages the endocardium at an angle. In this case, the countervailing force from the endocardium bends distal end 24 of the tube, and may also compress the distal end. As is explained in more detail below, embodiments of the present invention measure either type of deformation, due to head-on or angled engagement, and the measurements provide an indication of the direction and magnitude of the force, and also of the pressure, causing the deformation. (The measurements may also provide an indication of the deflection of termination 28.)

The pressure indication may be used by the operator of catheter 20 to ensure that termination 28 is pressing against the endocardium firmly enough, and in a required direction, to give the desired result, but not so hard or in a direction as to cause undesired tissue damage. U.S. Patent Application 20090093806, to Govari et al., filed Oct. 8, 2007, whose disclosure is incorporated herein by reference, describes a system that uses a pressure-sensing catheter in a similar manner. Catheter 20 may be used in such a system.

The deflection indication may be used by the operator to judge if termination 28 is correctly positioned.

Figure 2:
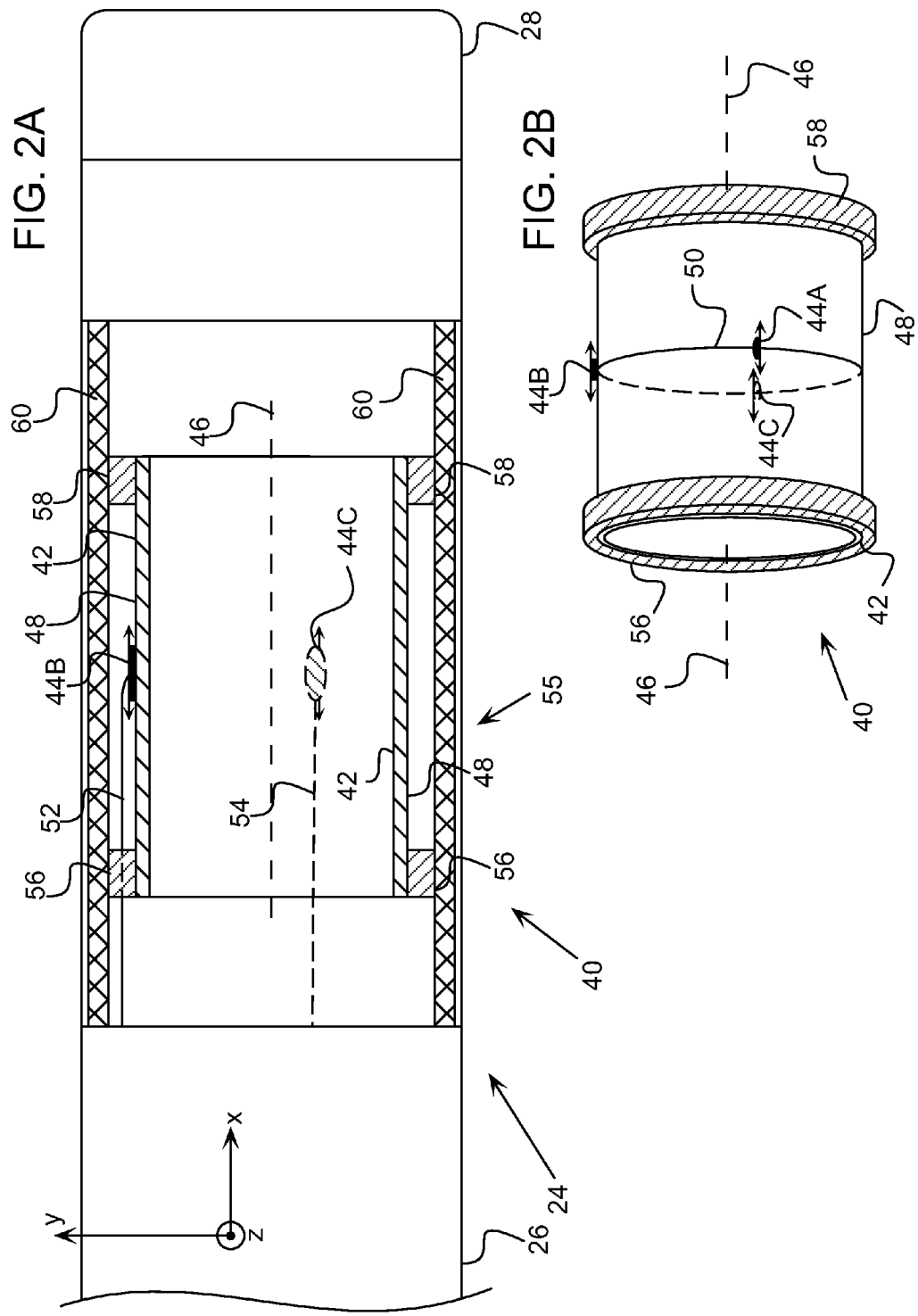
FIG. 2A is a schematic, cutaway view of the catheter, showing a pressure sensing assembly.
FIG. 2B is a schematic perspective view of the pressure sensing assembly, according to an embodiment of the present invention.

FIG. 2A is a schematic, cutaway view of catheter 20, showing a pressure sensing assembly 40 installed in distal end 24 of insertion tube 26, and FIG. 2B is a schematic perspective view of the pressure sensing assembly, according to an embodiment of the present invention. Pressure sensing assembly 40 comprises a thin-walled tube 42 of an elastic material, typically a metal material, and the tube is herein also referred to as sensor tube 42. The sensor tube is typically in the form of a hollow right circular cylinder, having an axis of symmetry 46. The elastic material forming the tube may comprise a superelastic alloy such as nickel titanium (Nitinol). For intracardiac applications, the overall length of tube 42 may be approximately 5 mm, with a wall thickness of approximately 0.1 mm, and an outer diameter of approximately 2 mm. Alternatively, in other applications, the dimensions of sensor tube 42 may be larger or smaller than those exemplified above.

For clarity, in the following description, sensor tube 42 is assumed to be oriented and aligned with a set of xyz orthogonal axes, as shown in FIG. 2A, (the x- and y-axes being in the plane of the paper) so that axis 46 is parallel to the x-axis. However, it will be appreciated that embodiments of the present invention may function in substantially any orientation.

A plurality of strain gauges 44A, 44B, 44C, . . . are fixedly attached to a surface 48 of sensor tube 42. In the following description, except where otherwise indicated, surface 48 is assumed to comprise the outer curved surface of tube 42. Strain gauges 44A, 44B, 44C, . . . are also referred to herein generically as strain gauges 44 and are also referred to as strain-measuring gauges 44.

Typically, strain gauges 44 are of generally similar types. A number of different types of strain gauges, i.e., gauges that provide an indication of the amount of deformation of a material, are known in the art. For example, strain gauges 44 may comprise metallic foil gauges or semiconductor gauges (the latter using a piezoresistive effect), which respectively indicate strain by a change in resistance of a metal or a semiconductor. Alternatively, strain gauges 44 may comprise other devices capable of providing an indication of strain, such as a piezoelectric crystal, which indicates strain according to a potential developed across the crystal in response to the strain, or a fiber optic, which indicates strain by a change in a characteristic of the fiber optic, such as a resonant wavelength of a diffraction grating formed in the fiber optic. The fiber optic characteristic is typically evaluated by radiation transmitted through the fiber optic.

In the description and in the claims, the terms strain gauge and strain-measuring gauge are assumed to comprise any device, such as those exemplified above, which is able to provide an indication of strain. For simplicity, except where otherwise indicated, in the following description strain-measuring gauges 44 are assumed to comprise metallic foil gauges.

Strain gauges typically measure strain in a particular direction, herein termed the "gauge direction," relative to the gauge. In the figures, the gauge direction for a particular gauge is indicated by a double-headed arrow adjoining the symbol for the gauge. Thus, by way of example and as shown in FIGS. 2A and 2B, strain gauges 44 have a common alignment, so that their gauge directions are parallel to the x-axis. However, there is no requirement that the gauge direction of strain gauges 44 have a common alignment, and in some embodiments the gauge directions are different.

In the following description of a disclosed embodiment, there are assumed to be three strain-measuring gauges 44A, 44B, and 44C, which are symmetrically disposed with respect to sensor tube 42. It will be understood that such a symmetric disposition of the strain gauges with respect to the sensor tube facilitates determining the magnitude and direction of the pressure exerted on termination 28, as well as the magnitude and direction of the deflection of the termination, regardless of the direction of the pressure. Also in the disclosed embodiment, strain gauges 44A, 44B, and 44C are fixedly attached to tube 42 on a common circumference 50 of an outer surface of the tube. Common circumference 50 is typically approximately centrally positioned with respect to tube 42, and is orthogonal to axis 46 so that it lies in a yz plane. It will be understood that central positioning of circumference 50 typically enhances values read from gauges 44 for a given pressure on termination 28.

The attachment of the gauges may be implemented using any convenient bonding material, such as a cyanoacrylate based adhesive. The gauges are typically attached so that they are disposed symmetrically on circumference 50, and so that their gauge directions are as described above, i.e., parallel to the x-axis.

However, in other embodiments of the present invention, the plurality of strain-measuring gauges 44 may comprise any integral number greater than or equal to 2, and there is no requirement that the plurality be disposed symmetrically with respect to tube 42. An embodiment with an asymmetric disposition of strain gauges is described with reference to FIG. 5 below.

Each strain gauge 44 is typically connected by respective cabling to processing unit 23 (FIG. 1). In FIG. 2A, cabling 52 to gauge 44B and cabling 54 to gauge 44C are shown. The cabling to strain gauges 44 is also referred to herein generically as cabling 55. Depending on the type of strain gauge, cabling 55 may typically comprise a twisted-pair cable or a fiber optic cable. Signals are transferred via the cabling to processing unit 23, which is configured to analyze the signals so as to determine the strain of each gauge.

Insertion tube 26 of the catheter comprises an outer flexible tubular sheath 60, which encloses operative portions of the catheter. The operative portions include elements such as conductive cabling and/or fluid-carrying tubing and/or pull-wires to guide catheter 20. For simplicity, these operative portions of the catheter are not shown in FIG. 2A. Sheath 60 typically comprises a composition of plastic with strengthening elements, such as metallic wiring, included in the composition.

Pressure sensing assembly 40 is fixedly attached to sheath 60. By way of example, the attachment is assumed to be implemented by two generally similar rings 56, 58. Rings 56, 58 have internal diameters equal to the external diameter of sensor tube 42, and external diameters equal to the internal diameter of sheath 60. Rings 56, 58 are typically positioned at respective ends of the sensor tube. During positioning, assembly 40 may be fixedly attached to sheath 60 by application of an adhesive or cement to the internal and external circumferences of rings 56, 58. Rings 56, 58 are typically configured so that, on attachment of assembly 40 to sheath 60, the assembly is symmetrically disposed with respect to the sheath, i.e., with respect to distal end 24.

Rings 56, 58 are one possible method by which assembly 40 is fixedly attached to sheath 60. Those having ordinary skill in the art will understand that other methods for attachment, for example using a plurality of spacers between the assembly and the sheath, may be used instead of, or in addition to, rings 56, 58. All such methods are assumed to be comprised within the scope of the present invention.

Once assembly 40 has been fixedly installed in distal end 24, the assembly may be calibrated, prior to the catheter being used for an invasive procedure such as that described above. The calibration comprises applying forces, that are known in both magnitude and direction, to distal end 24, typically by applying such forces to termination 28. In the following description, it is assumed that the known forces are converted to corresponding known pressures, using an effective area of termination 28 upon which the forces are applied. The applied known pressures include ranges of head-on pressures, as well as ranges (in magnitude and direction) of angled pressures, and the pressures cause corresponding deformations in sensor tube 42. For each known pressure, measurements of the strain generated by gauges 44 attached to the sensor tube are recorded and stored as calibration parameters of catheter 20, for example as look-up table 27 in memory 25.

The applied known pressures generate corresponding respective deflections of termination 28. The deflections may be measured, in both direction and magnitude, and are assumed, by way of example, to also be incorporated in the calibration parameters of catheter 20.

It will be understood that the calibration procedure described above, i.e., generating a look-up table, is one of a number of methods that may be used to calibrate assembly 40.

Other methods for calibrating the assembly will be familiar to those having ordinary skill in the art. For example, a first function relating the magnitude of the pressure to the values of strain of gauges 44, and a second function relating the direction of the pressure to the values of strain of the gauges 44, may be formulated. Typically, both functions are in the form of polynomials having the values of the strains of gauges 44, as well as higher powers of the strain values, as variables of the polynomials, each variable being multiplied by a respective coefficient. Similar functions may be formulated for the deflections of termination 28. The calibration procedure described above is used to determine the values of the coefficients for the respective functions, typically by applying a fitting procedure to the functions.

The equations and coefficient values determined in the calibration may be stored in memory 25 as the calibration parameters referred to above.

All calibration methods such as those described above are assumed to be comprised within the scope of the present invention.

During an invasive procedure such as is exemplified above, processing unit 23 determines "raw" values of strain measured by each of gauges 44. The processing unit accesses the calibration parameters stored in memory 25, in order to evaluate from the raw strain values, values of the magnitude and the direction of the pressure on termination 28, as well as values of the magnitude and direction of the deflection of the termination. The determined values may be provided to the operator of catheter 20, typically as part of a graphic user interface displayed on console 21.

The determination of the values of the magnitude and the direction of the pressure, and of the deflection, by processing unit 23 typically involve operations on the raw values, such as smoothing and/or filtering. In addition, depending on the type of calibration parameters, further operations may be required, For example, if the calibration comprises look-up table 27, processing unit 23 may apply an operation such as interpolation or extrapolation to determine, from the measured strain values of gauges 44, the direction and magnitude of the pressure on termination 28, and/or of the deflection of the termination. All such operations will be familiar to those having ordinary skill in the art, and are assumed to be included within the scope of the present invention.

Figure 3:
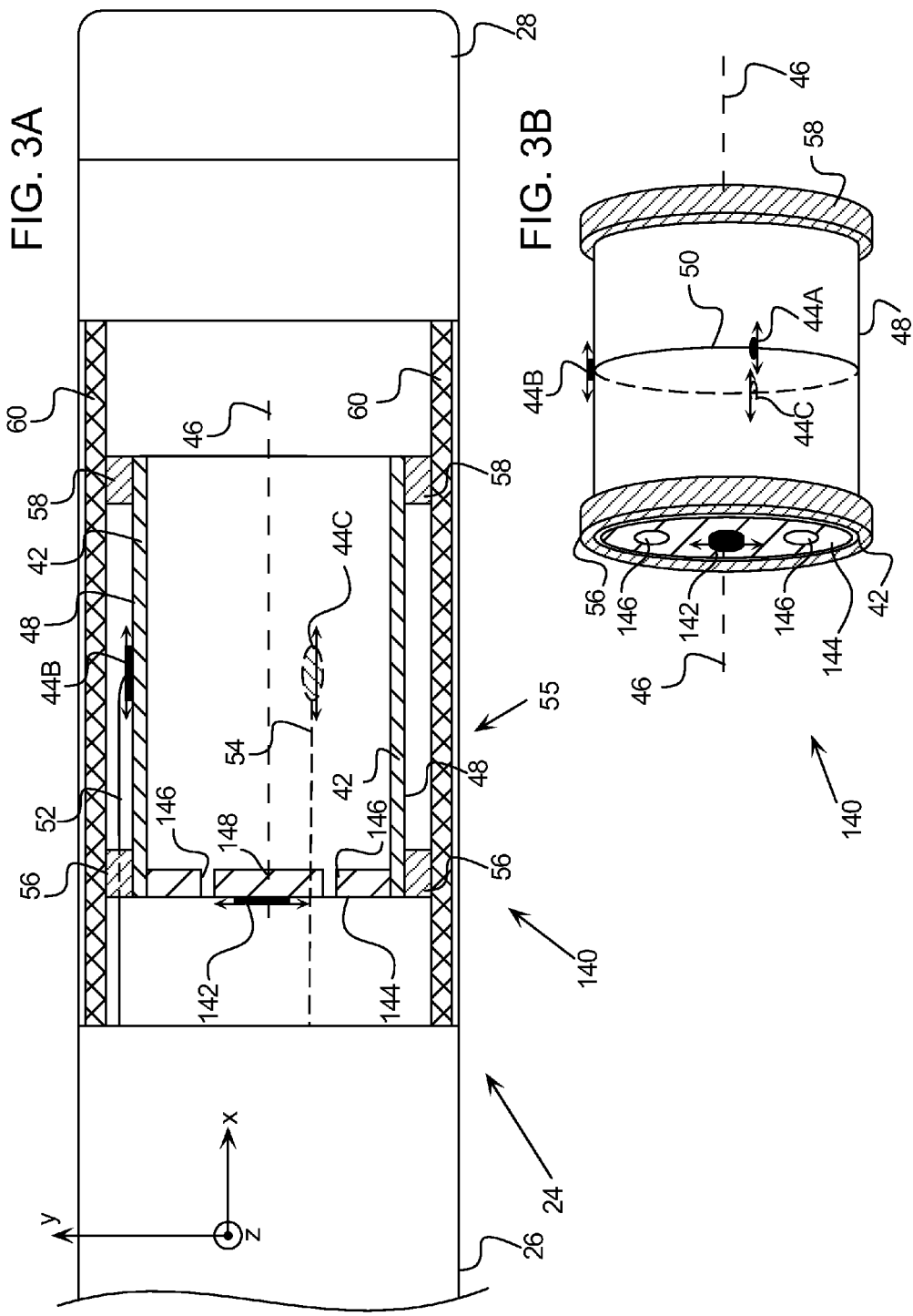
FIG. 3A is a schematic, cutaway view of the catheter, showing an alternative pressure sensing assembly.
FIG. 3B is a schematic perspective view of the alternative pressure sensing assembly, according to an embodiment of the present invention.

FIG. 3A is a schematic, cutaway view of catheter 20, showing a pressure sensing assembly 140 installed in distal end 24 of insertion tube 26, and FIG. 3B is a schematic perspective view of the pressure sensing assembly, according to an alternative embodiment of the present invention. Apart from the differences described below, the operation of assembly 140 is generally similar to that of assembly 40 (FIGS. 2A and 2B), and elements indicated by the same reference numerals in both assemblies 40 and 140 are generally similar in construction and in operation.

Readings from strain gauges 44 may be sensitive to temperature changes of the gauges. Because of its dimensions, sensor tube 42 has a low thermal mass, so that any changes in the ambient temperature around the tube typically cause corresponding changes in the temperature of gauges 44, affecting the accuracy of the values read from the gauges. Assembly 140 enables processing unit 23 to compensate for these changes, by incorporating one or more temperature-compensating strain gauges 142 in the assembly. Typically, gauges 142 are the same type of gauges as gauges 44, and are coupled by cabling similar to cabling 55 to PU 23. For simplicity, in FIGS. 3A and 3B only one temperature-compensating gauge 142 without cabling is shown.

In the alternative embodiment described herein, temperature-compensating gauges 142 are assumed to be mounted on a block 144, which has a thermal mass that is typically approximately the same as that of sensor tube 42. However, block 144, in contrast to tube 42, is configured and positioned in assembly 140 to be relatively inflexible when distal end 24 deforms. In addition, the gauge direction of temperature-compensating gauges 142 are typically set to be orthogonal to the gauge directions of gauges 44, so that in the embodiment described herein, the gauge directions of gauges 142 are orthogonal to axis 46. Thus, temperature-compensating gauges 142 have approximately the same temperature changes as gauges 44, but do not respond to the strains measured by gauges 44.

By way of example, block 144 is assumed to be a disk, having an external diameter equal to the internal diameter of tube 42. The block may be fixedly attached to sensor tube 42, for example, as illustrated in FIGS. 3A and 3B, by being positioned at the proximal end of the sensor tube, with a disk axis 148 congruent with axis 46. This arrangement facilitates the positioning of temperature-compensating gauges 142 so that their gauge directions are orthogonal to the gauge directions of gauges 44. Typically, block 144 comprises one or more apertures 146, which may be used to allow passage of elements such as cabling through sensor tube 42. In addition, the dimensions of apertures 146 may be adjusted so that the thermal mass of block 144 is approximately the same as that of tube 42.

Assembly 140 is calibrated substantially as described above for assembly 40. However, rather than using the "raw" values from strain gauges 44, as are used by processing unit 23 to calibrate assembly 40, the processing unit typically uses values of differences between strain-measuring gauges 44 and temperature-compensating strain gauges 142 to generate calibration parameters for assembly 140. Once the calibration of assembly 140 has been performed, during a procedure such as is described above, processing unit 23 typically uses difference values between the two types of gauges, and the assembly 140 calibration parameters, to determine the magnitude and direction of the pressure being applied to termination 28, as well as the deflection of the termination.

Figure 4:
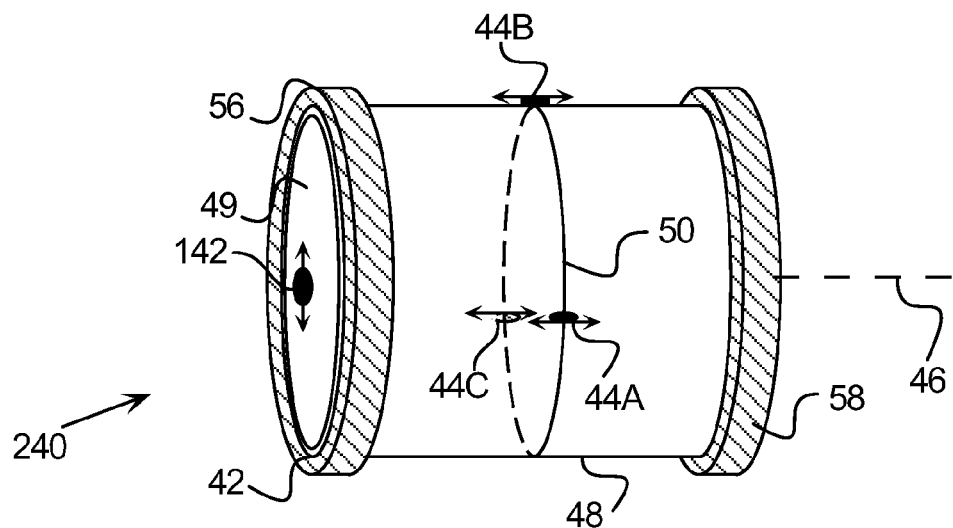
FIG. 4 is a schematic perspective view of a further alternative pressure sensing assembly, according to an embodiment of the present invention.

FIG. 4 is a schematic perspective view of a pressure sensing assembly 240, according to a further alternative embodiment of the present invention. Apart from the differences described below, the operation of assembly 240 is generally similar to that of assembly 140 (FIGS. 3A and 3B), and elements indicated by the same reference numerals in both assemblies 140 and 240 are generally similar in construction and in operation. Assembly 240 is typically installed within distal end 24 of catheter 20, substantially as is described above for assembly 140 (FIG. 3A).

In assembly 240, in contrast to assembly 140, temperature-compensating gauges 142 are not mounted on block 144, and the block does not form part of assembly 240. Rather, in assembly 240, gauges 142 are mounted on, or in proximity to, a region of sensor tube 42 that is not subject to the strains measured by gauges 44. Such regions, by way of example, comprise the ends of sensor tube 42, where the tube is fixedly attached to sheath 60 by rings 56, 58 (FIGS. 3A and 3B). Thus, as is exemplified by one temperature-compensating gauge 142 illustrated in FIG. 4, gauges 142 may be mounted on an internal curved surface 49 of sensor tube 42, close to the proximal end of the tube. Alternatively or additionally, at least some gauges 142 may be mounted on outer curved surface 48, close to the proximal end of the sensor tube; in some cases the mounting may be beneath rings 56 or 58 by providing a recess in the rings.

As for assembly 140, in assembly 240 temperature-compensating gauges 142 are typically oriented so that their gauge directions are orthogonal to the gauge directions of strain gauges 44.

Figure 5:
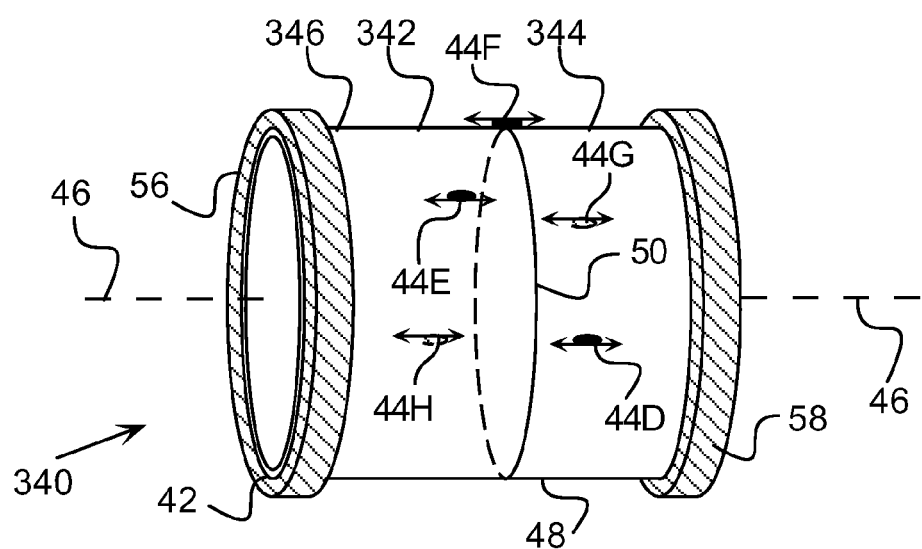
FIG. 5 is a schematic perspective view of a yet further alternative pressure sensing assembly, according to an embodiment of the present invention.

FIG. 5 is a schematic perspective view of a pressure sensing assembly 340, according to a yet further alternative embodiment of the present invention. Apart from the differences described below, the operation of assembly 340 is generally similar to that of assembly 40 (FIGS. 2A and 2B), and elements indicated by the same reference numerals in both assemblies 40 and 340 are generally similar in construction and in operation. Assembly 340 is typically installed within distal end 24 of catheter 20, substantially as is described above for assembly 40 (FIG. 2A).

By way of example, in assembly 340 strain-measuring gauges 44 are assumed to comprise five gauges 44D, 44E, 44F, 44G, and 44H. In contrast to assembly 40, in assembly 340 the five strain gauges 44 are not mounted on sensor tube 42 symmetrically. Rather, gauges 44D, 44E, 44F, 44G, and 44H are mounted in an asymmetric manner on the tube. Such an asymmetric disposition of gauges 44 with respect to the sensor tube may allow greater flexibility in positioning the strain gauges compared to a symmetric arrangement. Typically, gauges 44 are evenly distributed on either side of circumference 50, i.e., in a positive or a negative direction parallel to axis 46, with respect to the circumference. However, there is no necessity for such an even distribution, and an uneven distribution may be implemented in some embodiments.

The angles subtended by adjacent strain gauges 44 with axis 46, measured orthogonally to the axis, may be set to be approximately equal. The equalization of the angles facilitates determining the pressure exerted on termination 28 regardless of the direction of the pressure, as well as facilitating determining the deflection of the termination regardless of the pressure direction.

In some embodiments of the present invention, it may be desirable to measure the pressure exerted on termination 28, and/or the termination's deflection, if the pressure is in one or more predetermined directions. For example, catheters known in the art have pull-wires that bend the catheter in one or more particular predetermined directions. Embodiments of the present invention allow for measuring the pressure and the deflection in a predetermined direction by appropriate positioning of gauges 44.

For example, gauges 44E and 44D may be respectively repositioned to locations 342 and 344 on surface 48 of tube 42, the locations being selected so that gauges 44E, 44F, and 44D lie on a line 346 of surface 48, where line 346 is parallel to axis 46. Such an arrangement of gauges typically enables processing unit 23 to measure deformation of distal end 24 in predetermined directions, defined by being within the plane comprising line 346 and axis 46, more accurately than if gauges 44E and 44D are not repositioned. The pressure on, and/or the deflection of, termination 28 may consequently be measured more accurately. Other arrangements of gauges 44 on tube 42, for measurement of deformation of distal end 24 in a predetermined direction, will be apparent to those having ordinary skill in the art, and all such arrangements are assumed to be within the scope of the present invention.

It will be understood that features described above may be combined in ways that are not specifically described. As a first example, temperature-compensating gauges, such as are described with reference to assemblies 140 and 240, may be incorporated into assembly 340. As a second example, strain-measuring gauges, in assemblies such as assembly 340, may be arranged so that they are able to measure pressure substantially regardless of direction, and additionally or alternatively in one or more predetermined directions.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A medical probe, comprising:
 a flexible insertion tube, having a distal end for insertion into a body cavity of a patient and which is configured to be brought into contact with tissue in the body cavity; a sensor tube comprising an elastic material, contained inside the distal end of the insertion tube and configured to deform in response to forces exerted by the tissue on the distal end;
 a plurality of strain gauges fixedly attached to a surface of the sensor tube at different, respective locations and configured to generate respective signals in response to deformations of the sensor tube; and
 at least one temperature-compensating strain gauge configured to generate signals to compensate for changes in temperature of the plurality of strain gauges, wherein the at least one temperature-compensating strain gauge is mounted on a block having a block-thermal mass, and wherein the sensor tube has a sensor-tube-thermal mass equal to the block-thermal mass.

2. The probe according to claim 1, wherein the sensor tube is fixedly attached inside the distal end to the insertion tube.

3. The probe according to claim 1, wherein the surface of the sensor tube comprises an outer curved surface of the sensor tube.

4. The probe according to claim 1, wherein the respective signals are configured to generate a magnitude and a direction of a pressure on a termination of the distal end.

5. The probe according to claim 1, wherein the respective signals are configured to generate a magnitude and a direction of a deflection of a termination of the distal end.

6. The probe according to claim 1, wherein the plurality of strain gauges are symmetrically disposed with respect to an axis of the sensor tube.

7. The probe according to claim 1, wherein the plurality of strain gauges are positioned on a circumference of the surface of the sensor tube, and wherein the circumference is centrally located with respect to the sensor tube.

8. The probe according to claim 1, wherein the plurality of strain gauges have respective gauge directions, and wherein the gauges are fixedly attached to the surface of the sensor tube so that the respective gauge directions are parallel to an axis of the sensor tube.

9. The probe according to claim 1, wherein the at least one temperature-compensating strain gauge is mounted on the block in a location that does not deform in response to deformations of the sensor tube.

10. The probe according to claim 1, wherein the at least one temperature-compensating strain gauge has a temperature-compensating strain gauge direction configured to be orthogonal to an axis of the sensor tube.

11. A method for producing a medical probe, comprising:
providing a flexible insertion tube, having a distal end for insertion into a body cavity of a patient and which is configured to be brought into contact with tissue in the body cavity; installing a sensor tube comprising an elastic material inside the distal end of the insertion tube, the sensor tube being configured to deform in response to forces exerted by the tissue on the distal end;
fixedly attaching a plurality of strain gauges to a surface of the sensor tube at different, respective locations, the strain gauges being configured to generate respective signals in response to deformations of the sensor tube; and
providing at least one temperature-compensating strain gauge configured to generate signals to compensate for changes in temperature of the plurality of strain gauges, wherein, the at least one temperature-compensating strain gauge is mounted on a block having a block-thermal mass, and wherein the sensor tube has a sensor-tube-thermal mass equal to the block-thermal mass.

12. The method according to claim 11, wherein the sensor tube is fixedly attached inside the distal end to the insertion tube.

13. The method according to claim 11, wherein the surface of the sensor tube comprises an outer curved surface of the sensor tube.

14. The method according to claim 11, wherein the respective signals are configured to generate a magnitude and a direction of a pressure on a termination of the distal end.

15. The method according to claim 11, wherein the respective signals are configured to generate a magnitude and a direction of a deflection of a termination of the distal end.

16. The method according to claim 11, wherein the plurality of strain gauges are symmetrically disposed with respect to an axis of the sensor tube.

17. The method according to claim 11, wherein the plurality of strain gauges are positioned on a circumference of the surface of the sensor tube, and wherein the circumference is centrally located with respect to the sensor tube.

18. The method according to claim 11, wherein the plurality of strain gauges have respective gauge directions, and wherein the gauges are fixedly attached to the surface of the sensor tube so that the respective gauge directions are parallel to an axis of the sensor tube.

19. The method according to claim 11, wherein the at least one temperature-compensating strain gauge is mounted on the block in a location that does not deform in response to deformations of the sensor tube.

20. The method according to claim 11, wherein the at least one temperature-compensating strain gauge has a temperature-compensating strain gauge direction configured to be orthogonal to an axis of the sensor tube.

\* \* \* \* \*